(12) United States Patent
Thorne et al.

(10) Patent No.: US 6,224,576 B1
(45) Date of Patent: May 1, 2001

(54) SAFETY DEVICE FOR A NEEDLE HAVING TWO SHARPENED ENDS

(75) Inventors: Gale H. Thorne; Craig N. Thorne, both of Bountiful, UT (US)

(73) Assignee: Specialized Health Products, Inc., Bountiful, UT (US)

( * ) Notice: Subject to any disclaimer, the term of this patent is extended or adjusted under 35 U.S.C. 154(b) by 0 days.

(21) Appl. No.: 09/434,416

(22) Filed: Nov. 4, 1999

(51) Int. Cl.[7] .................................................. A61M 5/00
(52) U.S. Cl. ........................... 604/198; 604/263; 600/576
(58) Field of Search .................................. 604/110, 192, 604/195, 198, 240–242, 263; 600/576–579; 128/898; 206/365

(56) References Cited

U.S. PATENT DOCUMENTS

| | | | |
|---|---|---|---|
| 5,139,489 | 8/1992 | Hollister | 604/192 |
| 5,147,303 | 9/1992 | Martin . | |
| 5,154,285 | 10/1992 | Hollister . | |
| 5,193,552 | 3/1993 | Columbus et al. . | |
| 5,246,428 | 9/1993 | Falknor . | |
| 5,254,099 | 10/1993 | Kuracina et al. | 604/198 |
| 5,256,153 | 10/1993 | Hake . | |
| 5,356,392 | 10/1994 | Firth et al. | 604/198 |
| 5,403,283 | 4/1995 | Luther . | |
| 5,480,385 | 1/1996 | Thorne et al. | 604/110 |
| 5,487,734 | 1/1996 | Thorne et al. | 604/195 |
| 5,542,927 | 8/1996 | Thorne et al. . | |
| 5,549,708 | 8/1996 | Thorne et al. | 604/110 |
| 5,573,510 | 11/1996 | Isaacson . | |
| 5,823,997 | 10/1998 | Thorne . | |
| 5,980,488 | 11/1999 | Thorne | 604/110 |

*Primary Examiner*—Anhtuan T. Nguyen
(74) *Attorney, Agent, or Firm*—Paul S. Evans; Gale H. Thorne (57) ABSTRACT

A safety device for a phlebotomy needle having two sharpened tips, a forward or distal tip which is used for percutaneous sampling and a rear or proximal tip which is used to penetrate vacuum sampling tube stoppers. The phlebotomy needle safety device has a needle shield disposed about the rear or proximal needle, which is displaced only by the standard action of threadably connecting the device to a phlebotomy barrel, to permit penetration of vacuum sampling tube stoppers. The device also has a retractable and extendable, protective medical needle shield which provides opportunity for accessing and reaccessing a forward or distal needle and associated sharpened needle tip and recovering the needle and tip for safety between accesses. The shield includes a needle guide which assures the forward needle tip is untouched by any part of the shield as the shield is displaced to cover and uncover the needle.

5 Claims, 8 Drawing Sheets

SAFETY DEVICE FOR A NEEDLE HAVING TWO SHARPENED ENDS

FIELD OF INVENTION

This invention relates generally to safety devices for hollow bore medical needles and particularly to phlebotomy and other like medical safety devices employing needles having two sharpened ends.

PRIOR ART

Problems associated with inadvertent needle sticks are well known in the art of blood sampling, percutaneous medication injection and other medical procedures involving uses of medical needles. Ever increasing attention is being paid to needle stick problems due to the contemporary sensitivity of exposure to AIDS, Hepatitis and other serious blood-borne diseases.

Commonly, procedures involving removing a needle from a patient require a technician to use one hand to place pressure at the wound site where the needle is being withdrawn while removing the needle apparatus with the other hand. It is common practice for a tending technician to give higher priority to care for the wound than is given to disposal of a needle. In the case of commonly used, non-safety devices such priority either requires convenience of an available sharps container within ready reach or another means for safe disposal without leaving the patient's side. Providing adequate care, with accompanying safety procedures, is often compounded by patient condition and mental state (e.g. in burn units and psychiatric wards). Under such conditions, it is often difficult, if not impossible, to take appropriate procedures to properly dispose of a used, exposed needle while caring for a patient.

Widespread knowledge and history associated with needle care and disposal problems have resulted in conception and disclosure of a large number of devices each of which represents an attempt to provide not only a solution to the problem of needle sticks, but also a device which is commercially viable (i.e. cost and price competitive with currently used non-safety devices).

Examples of disclosures of safety devices which protect needles by moving a protective shield over a sharp end of a syringe or other hollow bore medical needle are found in U.S. Pat. No. 5,823,997 issued Nov. 17, 1998 to David L. Thorne (Thorne), U.S. Pat. No. 5,348,544, issued Sep. 20, 1994 to Sweeney et al. (Sweeney), U.S. Pat. No. 5,246,428 issued Sep. 21, 1993 to Donald W. Falknor (Falknor), U.S. Pat. No. 5,256,153 issued Oct. 26, 1993 to Lawrence W. Hake (Hake) and U.S. Pat. Nos. 5,139,489 and 5,154,285, issued Aug. 18, 1992 and Oct. 13, 1992, respectively, to William H. Hollister (Hollister). There are many other examples of safety devices which retract needles into housings, however, this instant invention is more directly related to devices which extend a shield over a needle rather than to those which employ needle retraction.

Thorne discloses a safety needle enclosure which is disposed to rotate about a needle and, upon being displaced to a needle shielding state, forms a substantially rigid part in cooperation with the needle to thereby provide a safe needle shield. The enclosure comprises a plurality of rigid segments serially interconnected by a plurality of intersegment hinges, which are preferably living hinges The segments are disposed about a medical needle, folded upon each other during the medical procedure and extended at the end of the procedure to form a secure, substantially rigid safety shroud. During the procedure, the enclosure is folded and disposed about a proximal portion of the needle. At the end of the procedure, the enclosure is extended to protectively sheath and secure the needle in a substantially rigid structure formed by the combination of the enclosure and the needle. Reference is made to Thorne for clarifying disclosure of invention which may be related to some embodiments of the instant invention disclosed herein. Though embodiments of the instant invention employ safety enclosures similar to those disclosed in Thorne, the scope is well beyond the device envisioned and taught in Thorne.

Sweeney discloses a device comprising a shield and guard which are manually, slidably movable along a needle cannula from a site proximal to a user to a distal site where a needle tip is shielded. The device comprises a hinged arm which extends along the needle cannula and which is moved distally to collapse upon itself to extend the guard over the tip. Access to the tip is denied by a metallic clip. An alternative embodiment is also disclosed by which the manual operation is augmented by a spring. A device based upon Sweeney is currently being distributed by Becton Dickinson and Company, Franklin Lakes, N.J. in which three separate parts (two injection molded and one metal clip) are used to mechanize the shield. Once the device is extended to shield the needle tip, it cannot be easily reset to recover use of the needle for a subsequent procedure. Also, the hinged arm requires activation in the region of the needle itself and comprises parts which are of a size which occasionally impedes a user's line of sight to insertion locations. The device based upon Sweeney is not readily resettable from a safety condition to a reusable state.

Falkner, and related disclosures, disclose devices comprising shields which are automatically releasable to extend distally from a user to cover a needle. The devices comprise latch mechanisms which are manually switched between unlatched and latched positions to free the needle for use and lock the shield over the needle, respectively. Of course, position of the latch mechanism provides a visual interpretation of the safety of the device (i.e. whether or not a latch is engaged), but that is the only safety mechanism and a "missed" indicator of latch mechanism position may be possible in stressful circumstances. When the latch mechanism is in the unlatched position, access to the needle is not only possible, but likely when the front of the device is impacted by a body part. In addition, the shield, though made of transparent material, covers a portion of an attached syringe body until fully extended and may make reading portions of volume measurement indicia on the syringe body difficult to read with accuracy when the syringe is being used in a titrating application.

Hake is representative of disclosure of devices comprising a manually slidable guard which is disposed over a syringe body during a medical procedure involving a medical syringe needle and manually, slidably moved distally into a needle guarding position usually at the end of the procedure. Commonly users of such devices complain of difficulty of seeing measurement indicia while the guard is disposed over the syringe body and of danger of inadvertent needle sticks while sliding the guard distally to cover the needle. As well, it is generally difficult to determine whether a guard is in a locked or unlocked state when it covers the needle, making an additional possibility of inadvertent needle sticks.

Hollister discloses a needle protection device which may be used with a double-ended needle assembly or with a simpler single needle system. The protection device comprises a substantially rigid housing flexibly connected to a container (for a vacuum tube sampling system) or to a needle hub. To exercise the protection device, the rigid member is pivotally rotated into engagement with an exposed needle of the double-ended needle assembly and is securely affixed to the exposed needle. A major drawback of the needle protection device of Hollister is the size and position of the rigid housing. During use of an assembly or system in a medical procedure, length and position of the housing member is considered by some to be inconvenient. A second drawback is the requirement either for two handed operation to pivot the housing to engage the needle or for the requirement to find and use a stable support surface against which the housing is pressed while the needle is swung into engagement with the housing. In a currently marketed format, an integral container holder version of the device disclosed by Hollister comprises two injection molded parts which permit the housing to be rotated, as much as possible, out of the way during a medical procedure. Such a format requires five injection molded parts, including a disposable needle assembly.

It is important to note that all of the art referenced above, and the majority of such devices in the safety needle field which relate to phlebotomy devices, are concerned with providing protection against sticks resulting from interaction with the forward or distal sharpened needle tip of the device unless a phlebotomy barrel is thrown away while still affixed to the needle. It is important to note that in phlebotomy there are two sharpened needle tips, the forward or sharpened needle tip for percutaneous entry and a rear or proximal needle tip for penetrating a vacuum tube stopper. The rear or proximal needle tip is normally disposed within a phlebotomy barrel during use and often considered to be more dangerous as it is commonly hidden by a blood valve which impedes blood flow when sampling tubes are removed from contact with the rear needle tip. This rear needle is comparatively safely protected by the barrel while the needle is in use and if the barrel is thrown away with the needle, but the rear needle is commonly removed from the barrel for disposal.

A number of devices (usually associated with sharps containers) have been placed on the market for the purpose of providing safe containment and eventual disposal of used phlebotomy needles. Some of the devices have special inserts which facilitate separation of the needle from the barrel and subsequent delivery of the used separated needle into a sharps disposal container. However, such procedures and devices, generally add operational steps, increase utilization cost and often result in a period of time during the disposal procedure when one or both needle tips are not protected. The inventors know of no known devices which provide a safety protection for both ends of the needle, much less protection for the rear needle. Especially, there are no known devices which provide such rear needle protection without adding additional steps, in addition to simply unthreading the needle from the barrel, to assure the rear needle is immediately protected at needle/barrel separation.

Generally, other than acceptance of the type of operation offered by such devices, commercial viability is dependent upon manufacturing cost. Purchase decisions in the area in which these devices are used are very cost sensitive. As earlier observed, if gains in either improvement in safety or in labor savings are not found to make a device sufficiently competitive with contemporary items currently on the market, those devices are usually not found to be commercially viable.

BRIEF SUMMARY AND OBJECTS OF THE INVENTION

In brief summary, the novel invention disclosed herein dramatically diminishes known major problems resulting from injury-related needle sticks which may occur at the end of a medical procedure, but, perhaps more important to general patient welfare, this invention provides opportunity for fabrication of a very low cost safety needle system which permits for disposing of a medical needle without undo hazard before placing the needle into an appropriate waste container.

In the present invention, a shield is disposed about a needle and tip to provide protection of the forward sharpened end. Any safety forward needle shield may be used within the scope of this invention. However, note in this disclosure a temporary, a device having a releasible latch is disclosed which may be disengaged to refold the shield and permit reaccess to the needle in a subsequent medical procedure. Once each procedure is complete, the shield is again extended and latched to provide a safety cover. Further, a lock should be provided for selectively permanently affixing the protective shield to thereby assure secured needle tip protection at the end of use.

In a preferred embodiment, the shield includes a needle guide, proximally disposed relative to the tip of a forward needle, which protects the forward needle tip, both, as the protective shield is displaced to cover and shield the needle and as the shield is removed to bare the needle for use. The needle guide is disposed and constrained to travel in alignment with the long axis of the needle, but constrained to facilitate movement of the shroud about the needle without contacting the needle tip.

Having a releasible needle shield yields an opportunity to provide a phlebotomy needle assembly which may be uniquely packaged for transport and later used with a reusable phlebotomy barrel. Of course, phlebotomy needle assemblies generally include a pair of sharpened needle points. A primary element of this invention is a protective shield which is passively released to bare the rear needle only when the phlebotomy needle assembly is inserted into the phlebotomy barrel. Having a combination of a releasible needle shield for the forward needle tip and a passive shield for the rear needle tip permits the needle to be packaged in a "soft package" for transport prior to use, thereby reducing cost and complexity of protective packaging components.

Other important factors in safety needle devices involve whether the device can be effectively used by a single hand and any extra steps involved in activating a safety mechanism. The act of threadably inserting each needle, made in accordance with the instant invention, into a barrel bares the rear needle tip for use. The act of unthreading the needle from the barrel protectively recovers the rear needle tip. Thus, the rear needle is passively protected. Protection of the forward needle tip is preferably accomplished by a single, one-handed step as taught by Thorne or Sweeney.

It is an important object to provide a safety phlebotomy needle device which has protective shields for both sharpened needle tips to provide protection before the needle affixed to a phlebotomy barrel and after the needle is removed from the barrel.

It is another important object to provide a phlebotomy needle device which can safely be packaged in a "soft package."

It is yet another important object to provide a needle guide which is disposed to operate within the shield to assure the sharp tip of the needle is untouched throughout each needle covering and baring procedure.

It is an object to provide a phlebotomy needle safety system wherein both sharpened needle tips are protected by removable shields.

It is an object to provide a removable shield on the distal end of a double ended phlebotomy needle by which the needle is reaccessible.

It is a further object to provide a safety shield, for the proximal end of a phlebotomy needle, which is passively removed when the needle is inserted into a phlebotomy barrel.

These and other objects and features of the present invention will be apparent from the detailed description taken with reference to accompanying drawings.

DETAILED DESCRIPTION OF THE ILLUSTRATED EMBODIMENTS

In this description, the term proximal is generally used to indicate relative nearness of a referenced item to a user of a device or a viewer. The term distal is similarly used to indicate relative remoteness. Reference is now made to the embodiments illustrated in FIGS. 1–8 wherein like numerals are used to designate like parts throughout.

Figure 1:
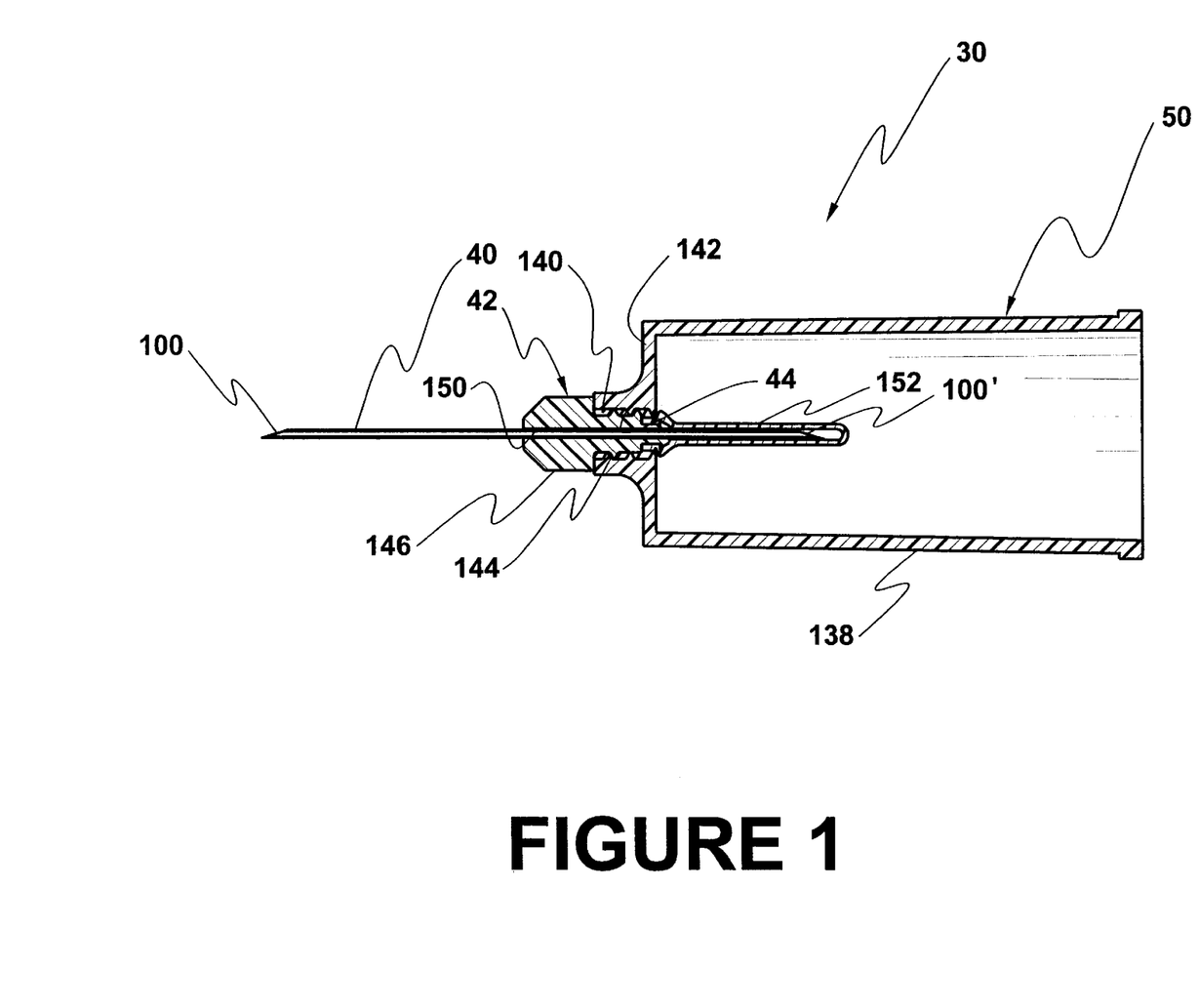
FIG. 1 is a cross section of a lateral view of a prior art phlebotomy device including a phlebotomy needle with proximal and distal sharpened ends, a needle hub, a blood valve and a phlebotomy barrel.

A phlebotomy device 30 which is representative of devices in current use is seen in FIG. 1. Device 30 generally utilizes a needle 40 having two sharpened ends, 100 and 100'. In this case, a hub 42 has a threaded connection 44 which may be used with a phlebotomy barrel, such as the phlebotomy barrel 50 seen in FIG. 1, and described in detail hereafter.

Figure 2:
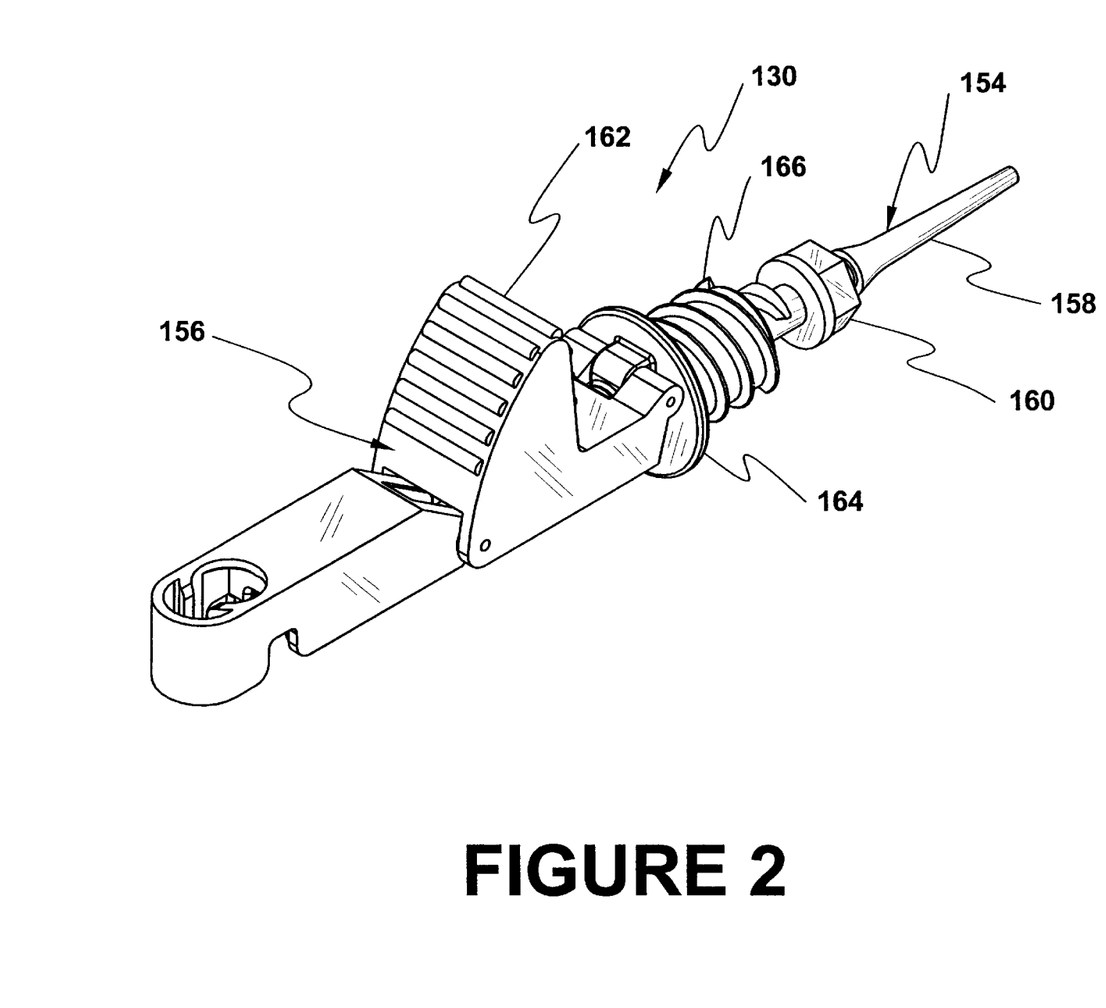
FIG. 2 is a perspective of a medical shield assembly for phlebotomy which provides protection for the proximal and distal tips of a phlebotomy needle.

Reference is now made to FIGS. 2 wherein another embodiment of a needle shield device 130 is seen. A cross sectional representation of a phlebotomy device 30 is provided in FIG. 1 to better disclose the inventive aspects of device 130. Phlebotomy device 30 is commonly assembled from two parts, a phlebotomy barrel 50 and a phlebotomy needle assembly 42. Phlebotomy barrel 50 generally consists of an elongated cylindrical barrel 138 and a needle assembly introduction port 140 distally disposed in an otherwise closed end 142. Port 140 has a female threaded connection 144 by which assembly 42 is securely affixed to barrel 50 for use.

Assembly 42 has a needle hub 146 comprising a male threaded connector 44 adaptable to female threaded connection 144. Hub 146 has an elongated bore hole 150 into which a medical needle 40 with its two sharpened ends 100 and 100' is inserted and securely affixed. End 100' commonly has a noncoring bevel for use in penetrating stoppers of a blood collection vacuum tube. To minimize uncontrolled blood flow when a blood collection vacuum tube is not attached to end 100', a blood valve 152 is usually affixed to hub 146 about a proximal portion of needle 40 and end 100'.

Commonly, a barrel, such as barrel 50, is provided separately from assembly 42, with both ends 100 and 100' of needle 40 protectively covered for transport and storage. Before interconnecting assembly 42 to barrel 50, a cover is removed from the end 100' and hub 146 is threadably affixed to barrel 50. Note that, during this procedure, needle tip 100' is unprotected. A cover is then removed from needle end 100 of needle 40 to prepare device 30 for use. Once used, assembly 42 is removed from barrel 50 and usually disposed of in a sharps container. For safety, it is becoming more common to shroud a used phlebotomy needle with a safety needle shield at the end of a medical procedure. However, proximal sharp needle points, such as needle end 100', are rarely if ever protected. Such lack of protection is often compensated for by special methods of disengaging a used needle assembly from a barrel while disposing the used needle assembly into a sharps container, but ready availability of sharp containers, cost of devices which provide for the special methods and actually properly performing the special methods every time a used needle is discarded puts universal proper disposal at risk.

Figure 3:
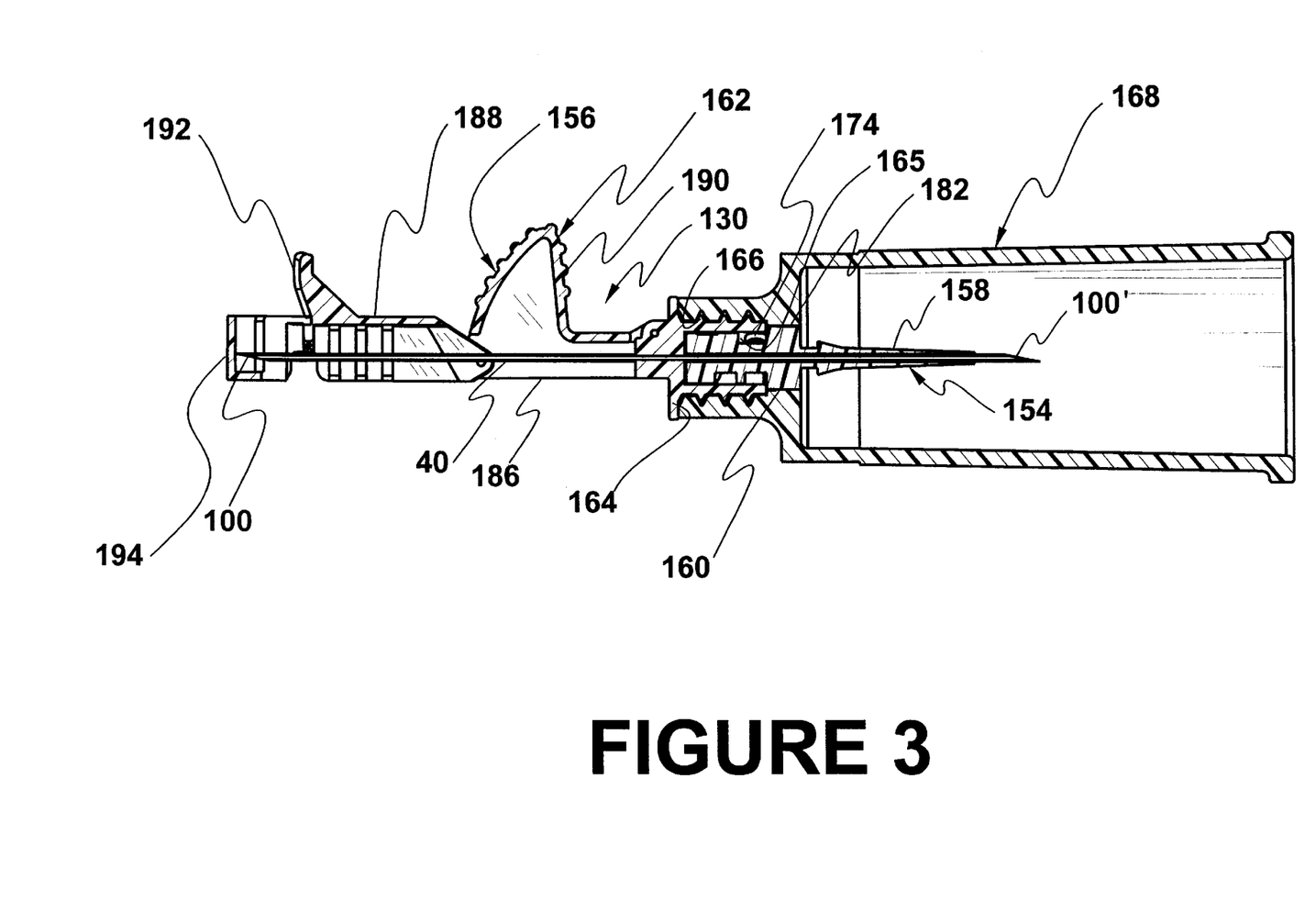
FIG. 3 is a lateral cross section of the medical shield assembly of FIG. 2 disposed in a phlebotomy barrel with a blood valve removed for clarity of presentation.
Figure 4:
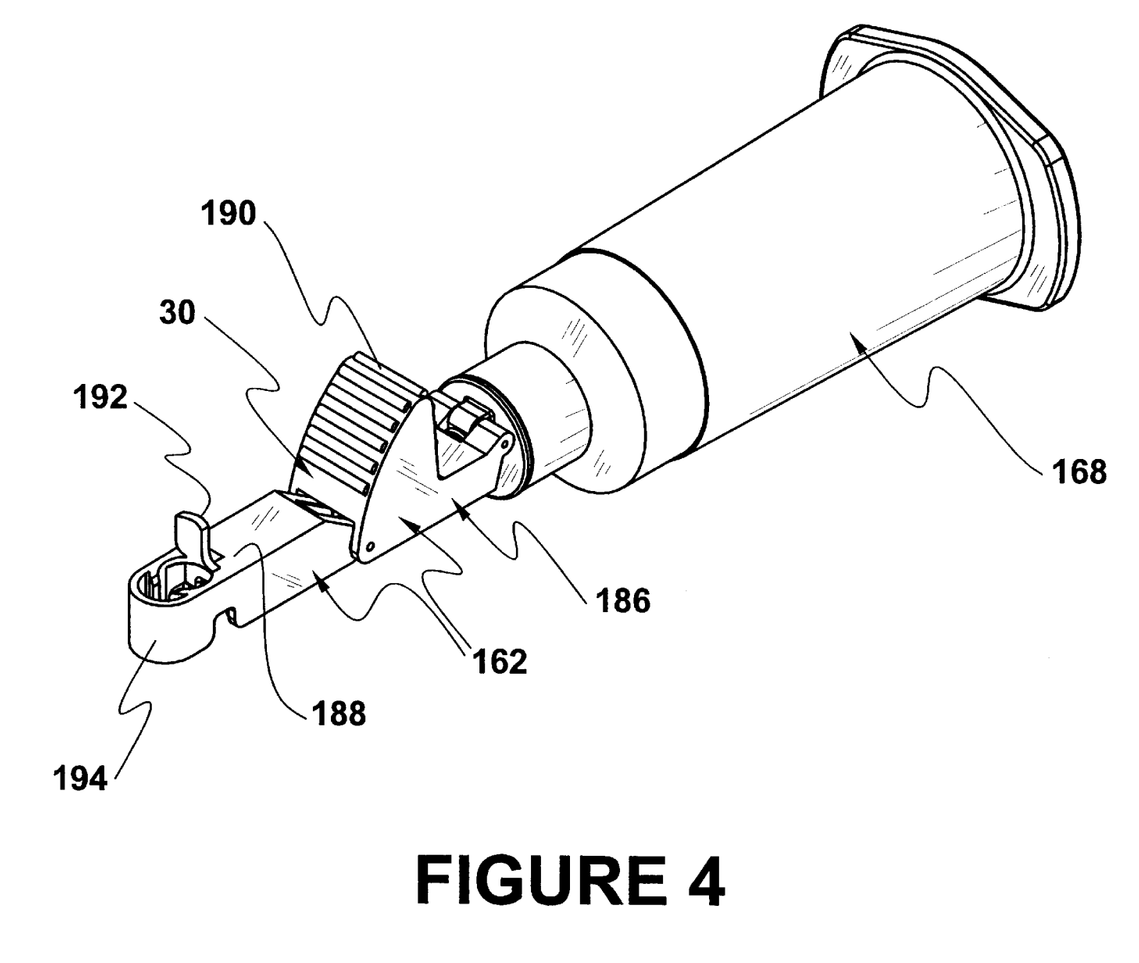
FIG. 4 is a perspective of the device seen in FIG. 3.
Figure 5:
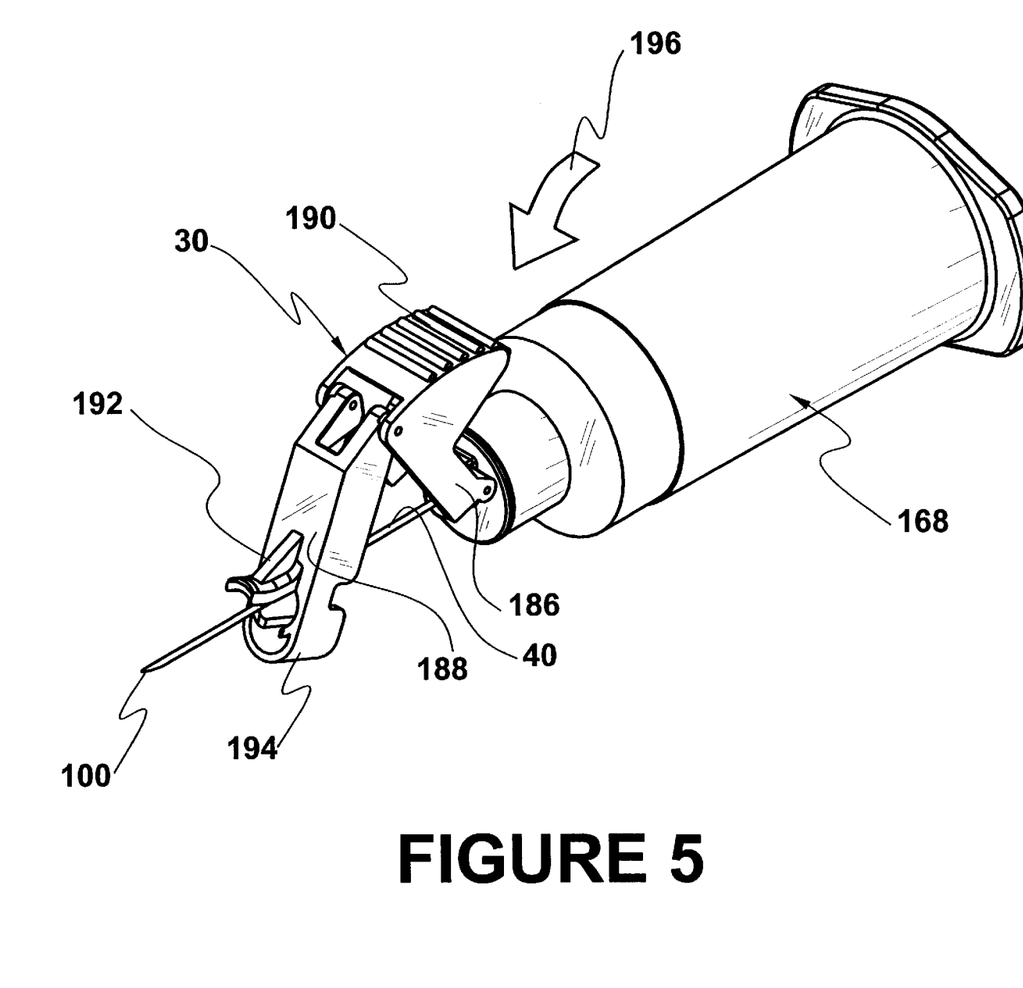
FIG. 5 is a perspective of the device seen in FIG. 4 having the shield assembly displaced to partially expose a needle disposed therein.

Referring again to FIG. 2, device 130 provides for protectively covering both sharp ends 100 and 100' of a double ended phlebotomy needle 40 (see FIG. 3). As seen in FIG. 3, device 130 is assembled from two parts, a rear needle protection component 154 and a forward needle-hub-shield assembly 156.

Component 154 has a rear needle shield 158 and an associated distally disposed fitting 160, the purpose and function of each of which shall be disclosed in full hereafter. Assembly 156 comprises a needle shield 162, which may otherwise be similar in form and function to shields of Thorne and Sweeney, earlier referenced, and a needle hub 164 to which a needle 40 is securely affixed. Hub 164 and needle 40 are seen in combination in FIG. 3. Similar to hub 146, hub 164 has a proximally disposed threaded section 166 for releasibly, but securely affixing device 130 to a phlebotomy barrel. Such a phlebotomy barrel 168 is seen in FIG. 3.

Figure 8:
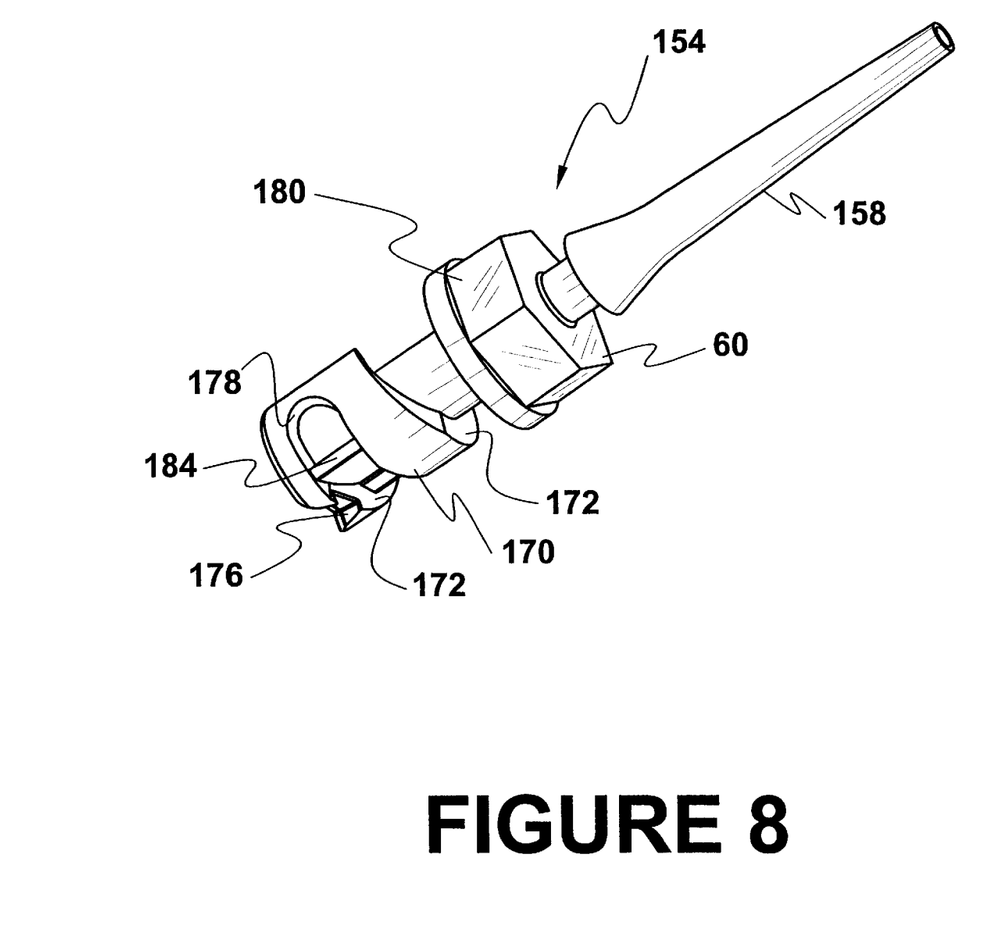
FIG. 8 is a perspective of a proximal needle shield of the device seen in FIGS. 2–6.

A perspective view of component 154 is seen in FIG. 8. Distally, component 154 has a threaded feature 170 having a sloped proximally disposed arcuate face 172 which has substantially the same pitch as threaded section 166 of hub 164, seen in FIG. 3. As seen in FIG. 3, hub 164 has a hollow cylindrical cavity 165 in which a knob 174 is medially disposed. Knob 174 is sized to fit within threaded feature 170 when component 154 is inserted into cavity 165 and to thereby constrain the therein inserted component 154 to threadably screw component 154 into cavity 165 as device 130 is threadably connected to barrel 168.

For initial assembly, feature 170 has a distally disposed slot 176 which is sufficiently large to permit knob 174 to be forcefully urged into engagement with threaded feature 170, but sufficiently small to resist facile extraction of knob 174 from feature 170. Further feature 170 comprises a blind end 178 which restricts knob 174 from being disengaged from feature 170 by unthreading.

Proximally disposed relative to feature 170 is a hex shaped connector 180. It should be noted that connector 180 may be any shape which may be linearly inserted into a complimentary receiving female connector, such as connector 182 (see FIG. 3). In this manner, component 154 is restricted from rotation as device 130 is threadably joined with a phlebotomy barrel, such as barrel 168, until hub 164 is fully seated into section 166. It is especially important to note that, as device 130 is threadably joined to phlebotomy barrel 168, feature 170 is likewise screwed into cavity 165, effectively shortening the length of device 130. This device shortening urges rear needle shield 158 distally relative to proximal needle tip 100', exposing tip 100' for use in piercing a stopper of a vacuum sampling tube. Note that in an unattached device 130, such as device 130 in FIG. 2, rear needle shield 158 protectively covers needle tip 100'. When device 130 is affixed to a barrel, such as barrel 168 in FIG. 3, rear needle shield 158 is displaced distally relative to tip 100', thereby exposing tip 100' for us in piercing vacuum sampling tube stoppers. When device 130 is threadably removed from barrel 168, device 130 is again lengthened, thereby covering needle tip 100' with rear needle shield 158 by restricting component 154 from rotating while device 130 is threadably detached. Thus, with a safety shield protectively disposed about needle tip 100 and with device 130 removed from barrel 168, both ends of needle 40 are protected as seen in FIG. 2.

Component 154 may be made as a single injection molded part from a synthetic resinous material such as polypropylene. In similar fashion, needle-hub-shield assembly 156 may also be made as a single injection molded part from polypropylene. Generally, medical needles, such as needle 40, are most commonly made from medical grade stainless steel.

Figure 7:
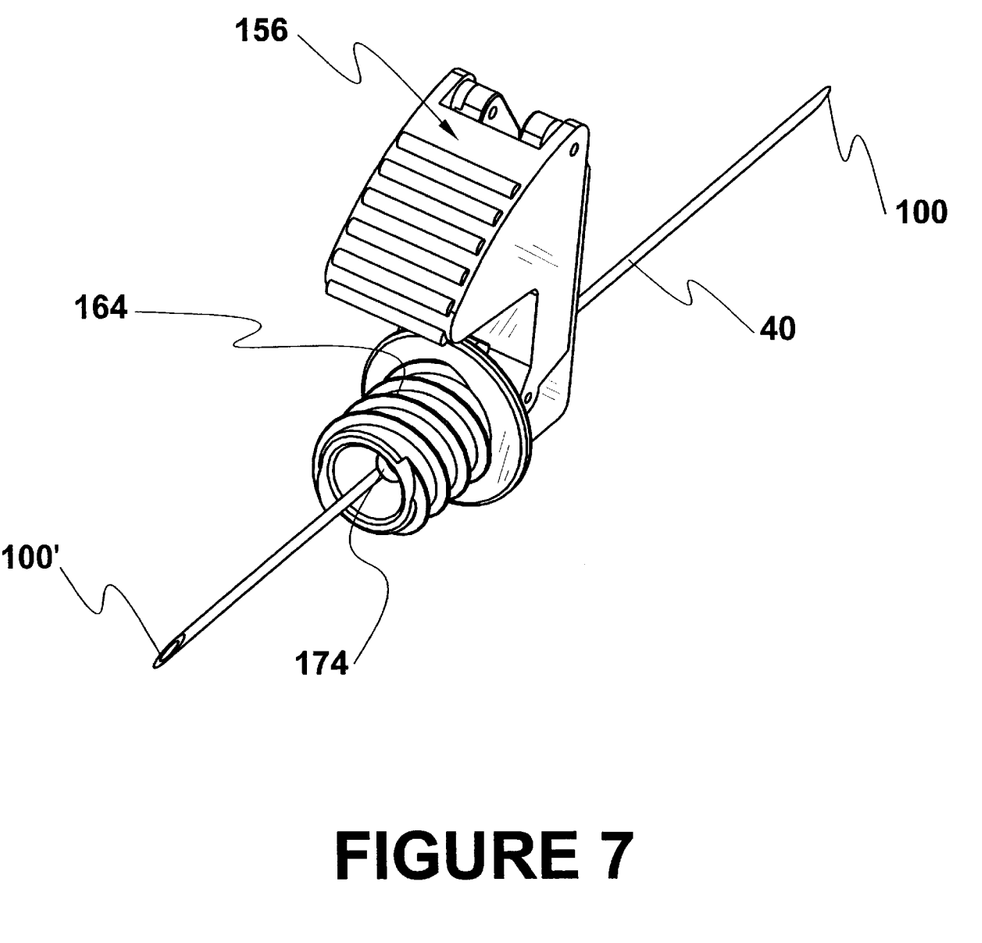
FIG. 7 is a perspective of a distal shield and hub section of the device seen in FIGS. 2–6.

To assemble device 130, needle 40 is securely affixed to hub 164 of needle-hub-shield assembly 156 as seen in FIG. 7. Then slot 176 (see FIG. 8) is disposed to receive knob 174. Component 154 is forcefully inserted to cause knob 174 to be displaced through slot 176 such that knob 174 resides in alignment with proximally disposed face 172. Once knob 174 is so disposed, device 154 may be rotated relative to assembly 156 to displace knob 174 across a raised stop 184 into contact with blind end 178 to provide a secure, but releasable transport state for device 130. Note that stop 184 is a bump raised to resist rotation of component 154 relative to assembly 156, but which is overcome by forces consistent with threading device 130 into barrel 168.

Referring again to FIG. 3, in addition to hub 164, assembly 156 is seen to comprise needle shield 162 having a proximal shield segment 186 and a distal shield segment 188. Of course, as earlier disclosed and as disclosed in Thorne, needle shields having different numbers of segments and other attributes such as needle/shield latches may be used within the scope of the invention.

Proximal segment 186 comprises an actuator button 190. Distal segment 188 has an appurtenance 192 which acts as a skid to prevent binding of shield 162 when actuator button 190 is depressed. No latch is seen in FIG. 3; however, latches, both releasable and unrelesible may be used in shields for device 130. In it is important to note that, in any event, each needle shield, e.g. shield 162, must be disposed in a substantially rigid state when covering a needle to effectively provide a protective cover. For this reason, when releasable latches are used, a positive action should be required to unlatch a shield to expose a needle for use. When so disposed the shield, e.g. shield 162, protects needle tip 100 by constraining needle 40 along its long axis and by distally enclosing tip 100 by a closed face 194.

Figure 6:
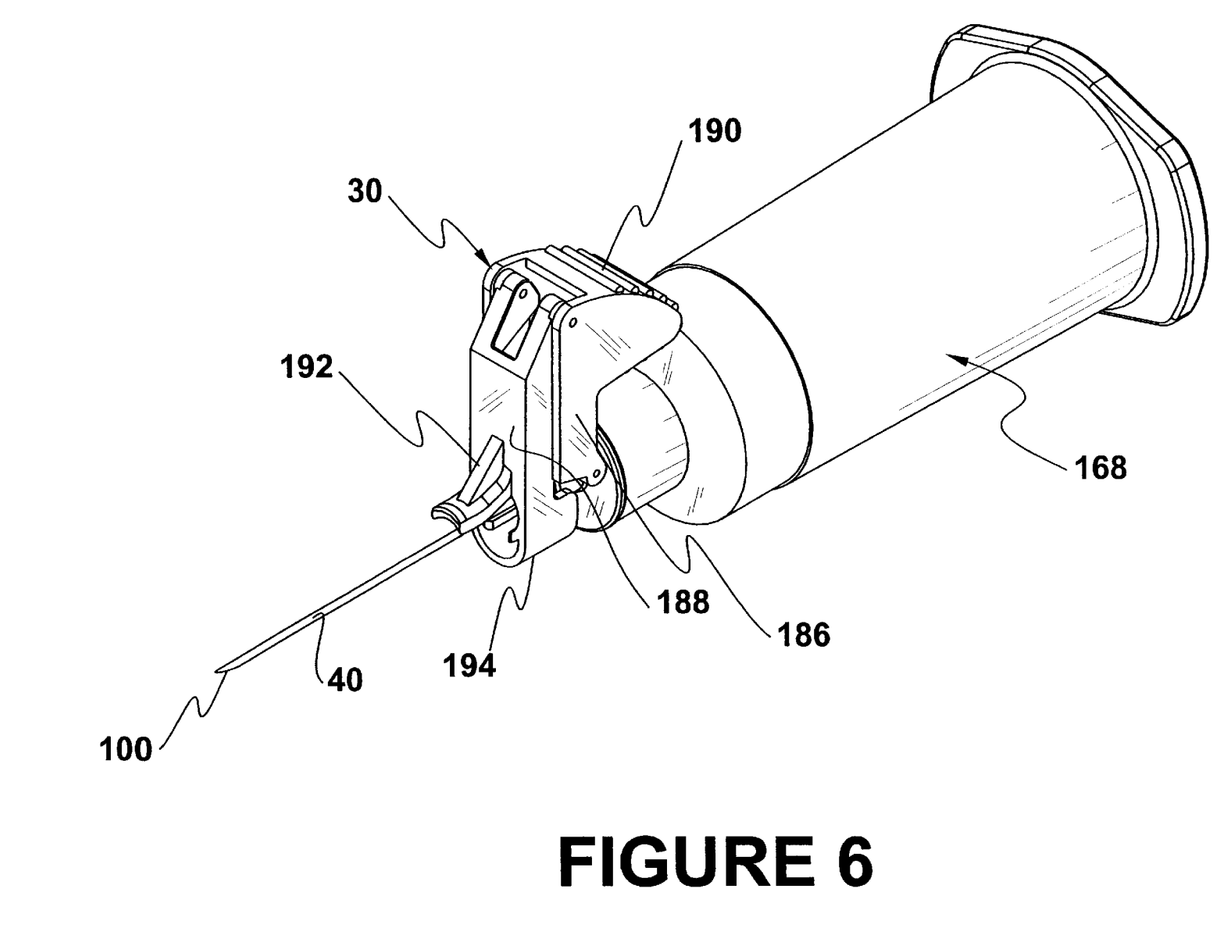
FIG. 6 is a perspective of the device seen in FIGS. 2 and 3 wherein the shield assembly is displaced to provide maximum exposure of the needle.

Reference is now made to FIG. 6 wherein an assembled combination of barrel 168 and device 130 are seen disposed ready for use. In this state, needle tip 100' is also bared for use as seen in FIG. 3. Depressing actuator button 190 in direction of arrow 196, seen in FIG. 5 extends shield 162. Shield 162 is seen to be fully extended in FIG. 4. Once shield 162 is fully extended, device 130, once again having safety shields employed over needle tips 100 and 100' may be removed from barrel 168 in a needle safety state.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety device for phlebotomy needles comprising:
   a phlebotomy barrel having a first female connector which threadably receives a complementary first male threaded connector of a phlebotomy needle hub assembly, said first female threaded connector further comprising a proximally disposed locking member which slidably engages and thereby resists rotation of a portion of the phlebotomy needle hub assembly as said phlebotomy needle hub assembly is being threadably affixed to said phlebotomy barrel;
   the phlebotomy needle hub assembly comprising:
      a phlebotomy needle having a forward, distally disposed sharpened tip and a rear, proximally disposed sharpened tip;
      a needle hub in which said phlebotomy needle is firmly affixed, said hub comprising:
         the first male threaded connector part having a diameter and pitch which is compatible with being threadably affixed to said first female barrel connector; and
         a second female threaded connector part disposed within said first male connector part, said second female threaded connector part having a diameter which is smaller than the first male connector part and a pitch which is substantially the same as the first male threaded connector part;
      a rear needle shield comprising a second male threaded connector part having a diameter and pitch which corresponds to the hub assembly second female threaded connector part and a rear shield having a length which protectively extends about and beyond the proximal sharpened tip when the phlebotomy needle hub assembly is disconnected from said phlebotomy barrel;
      said rear needle shield further comprising a fitting which is slidably displaced into said locking member when connection is made between the first male and female threaded connectors thereby causing said rear needle shield to resist rotation relative to the phlebotomy barrel as the rear needle assembly is threadably engaged with said phlebotomy barrel, resulting in said second male connector part being threadably engaged with the second female connector effectively shortening the rear needle assembly to bare the rear needle tip.

2. A safety device for phlebotomy needles according to claim 1 further comprising a safety shield which selectively provides protection for said forward, distally disposed sharpened tip.

3. A method for passively activating a safety shield for a needle shield for a phlebotomy needle device comprising the steps of:

provjding a phlebotomy barrel having a first female connector which threadably receives a complementary first male threaded connector of a phlebotomy needle hub assembly, said first female threaded connector further comprising a proximally disposed locking member which slidably engages and thereby resists rotation of a portion of the phlebotomy needle hub assembly as said phlebotomy needle hub assembly is being threadably affixed to said phlebotomy barrel;

providing the phlebotomy needle hub assembly comprising:
  a phlebotomy needle having a forward, distally disposed sharpened tip and a rear, proximally disposed sharpened tip;
  a needle hub in which said phlebotomy needle is firmly affixed, said hub comprising:
    the first male threaded connector part having a diameter and pitch which is compatible with being threadably affixed to said first female barrel connector; and
    a second female threaded connector part disposed within and aligned with said first male connector part, said second female threaded connector part having a diameter which is smaller than the first male connector part and a pitch which is substantially the same as the first male threaded connector part;

a rear needle shield comprising a second male threaded connector part having a diameter and pitch which corresponds to the hub assembly second female threaded connector part and a rear shield having a length which protectively extends about and beyond the proximal sharpened tip when the phlebotomy needle hub assembly is disconnected from said phlebotomy barrel;

said rear needle shield further comprising a fitting which is slidably displaced into said locking member when connection is made between the first male and female threaded connectors thereby causing said rear needle shield to resist rotation relative to the phlebotomy barrel as the rear needle assembly is threadably engaged with said phlebotomy barrel, resulting in said second male connector part being threadably engaged with the second female connector effectively shortening the rear needle assembly to bare the rear needle tip;

inserting the phlebotomy needle hub assembly with the rear shield disposed about and extended over the rear needle as a safety protector into the phlebotomy barrel and threadably affixing the phlebotomy needle hub assembly to the phlebotomy barrel and shortening the phlebotomy needle hub assembly to uncover the rear needle for use in a medical procedure; and after the procedure is finished, unthreading the phlebotomy needle hub assembly from the phlebotomy barrel, thereby restoring the rear shield about and over the needle to provide a safety protector as the rear needle tip is removed from the phlebotomy barrel.

4. A passively actuated safety device for a phlebotomy needle comprising:

a phlebotomy barrel which is threadably affixed to an otherwise separate phlebotomy needle hub assembly for the purpose of capturing physiologic samples in a blood sampling tube;

the phlebotomy needle hub assembly comprising:
  a phlebotomy needle having a forward, distally disposed sharpened tip and a rear, proximally disposed sharpened tip;
  a shield for the rear, proximally disposed sharpened tip, said shield being disposed to cover and protect the proximally disposed sharpened tip while the phlebotomy needle hub assembly is unattached to said phlebotomy barrel and being displaced to provide access by the blood sampling tube only when the phlebotomy needle hub assembly is affixed to phlebotomy barrel.

5. A passively actuated safety device for a phlebotomy needle according to claim 4 further comprising a safety shield for the forward, distally disposed needle tip.

* * * * *